(12) United States Patent
Vafi et al.

(10) Patent No.: US 6,713,769 B2
(45) Date of Patent: Mar. 30, 2004

(54) METHOD OF SENSING TEMPERATURE OF A DIGITAL X-RAY IMAGING SYSTEM

(75) Inventors: Habib Vafi, Brookfield, WI (US); Richard Gordon Cronce, New Berlin, WI (US); Scott William Petrick, Sussex, WI (US); Jeffrey Alan Kautzer, Pewaukee, WI (US); David Conrad Neumann, Milwaukee, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 127 days.

(21) Appl. No.: 09/683,738
(22) Filed: Feb. 7, 2002

(65) Prior Publication Data

US 2003/0146390 A1 Aug. 7, 2003

(51) Int. Cl.⁷ ................................................. G01T 1/24
(52) U.S. Cl. ................................................. 250/370.15
(58) Field of Search ..................................... 250/370.15

(56) References Cited

U.S. PATENT DOCUMENTS 5,970,113 A * 10/1999 Crawford et al. ............. 378/19
6,411,672 B1 * 6/2002 Sasaki et al. ................. 378/19

FOREIGN PATENT DOCUMENTS

JP 04315985 A * 11/1992 ............. G01T/1/20

* cited by examiner

Primary Examiner—Constantine Hannaher
(74) Attorney, Agent, or Firm—Peter J. Vogel

(57) ABSTRACT

An X-ray imaging system that utilizes the leakage, or dark current, of a detector panel's photodiodes to provide more accurate data about the temperature and spatial distribution of temperature of the X-ray detector panel. Offset images are taken at known temperatures and recorded for each photodiode at two or more known temperatures. A temperature versus offset image value curve is the created for each photodiode. A second offset image value is determined immediately prior to or immediately after X-ray acquisition to determine the temperature of the detector panel at the time of X-ray acquisition. A coupled closed-loop cooling system utilizes the determined temperature to maintain the detector panel within a preferred temperature range.

18 Claims, 5 Drawing Sheets

METHOD OF SENSING TEMPERATURE OF A DIGITAL X-RAY IMAGING SYSTEM

BACKGROUND OF INVENTION

The present invention relates generally to a digital X-ray imaging system and more specifically to a method of sensing temperature of a digital X-ray imaging system.

X-ray imaging systems, also known as X-ray detectors, have become essential in medical diagnostic imaging, medical therapy, and various medical testing and material analysis industries. One category of X-ray imaging systems uses scintillator materials located on an array of photodiodes and FET's to convert X-ray photons into visible-spectrum photons as part of the energy detection process. The photodiodes and FET's are located on a glass substrate panel. Since charge leakage from the diodes is an exponential function of temperature, the pixel outputs of the photodiodes and FET's are strongly dependent upon the temperature of the glass substrate panel.

For this reason, it is necessary to maintain the detector panel temperature within a narrow operating range, and to correct for images taken with the X-ray imaging system with an "offset image" taken without X-ray. The term "offset image" is used here to refer to an image that is taken from the X-ray imaging system without X-ray illumination, and which represents the output of the detector due to confounding factors including among other things diode leakage, charge retention, and electronic noise. Differences in digitized output values for a pixel's diode in an offset image that correlate differences in temperature of that pixel's diode are considered to be primarily due to diode leakage. Diode leakage is also known as dark current because it is the current the diode is passing while not illuminated.

Known detectors are cooled with liquid coolant flowing in a coldplate in the detector, with heat removed by a remotely mounted chiller. Temperature sensing is done with temperature sensors located on a circuit board in the detector near the glass substrate panel.

However, this type of temperature sensing has inherent errors. For example, the sensors are not in physical contact with the X-ray detector panel. Further, the number of sensors is limited both by cost and space available. Also, there are heat-dissipating components on the circuit boards which affect the temperature sensors. Thus, the temperature on the panel and the spatial distribution of temperature across the panel are known only approximately.

It is therefore highly desirable to provide a direct measure of the panel temperature and a better representation of the spatial distribution of temperature across the panel. Direct measurement of the panel temperature will enable improved closed-loop control of the detector cooling system. Knowledge of spatial distribution across the panel from direct measurement will enable the use of other cooling methods without the risk of some areas of the panel being outside the required temperature range for imaging.

SUMMARY OF INVENTION

The present invention uses the leakage (dark current) of the X-ray detector panel's diodes to provide more accurate data about the temperature of the X-ray detector panel.

To accomplish this, offset images are taken at known temperatures when the X-ray panel is manufactured. Offset values are recorded for each diode (pixel) at two or more known temperatures. A temperature versus offset curve is the created for each pixel. When the detector is installed into an imaging system, this data is loaded into the system for use by the imaging acquisition software. Upon subsequent use of the X-ray imaging system, values from the offset images, taken without X-ray either immediately before or immediately after the X-ray image are taken, are used with the temperature dependent coefficients of some or all of the diodes on the panel to calculate the temperature of the panel at the time of the offset image acquisition. The temperature of the panel and spatial distribution of temperature across the panel determined in this way may then used to regulate the cooling system of the detector to maintain the panel within the temperature range required for imaging.

This method will also allow for the use of cooling methods that are not presently available to known systems such as direct conduction cooling with heat pumped by thermoelectric coolers. This method also eliminates the need for thermal sensors on the circuit boards of the X-ray imaging system, which saves costs in terms of manufacturing and reliability.

Other objects and advantages of the present invention will become apparent upon the following detailed description and appended claims, and upon reference to the accompanying drawings.

DETAILED DESCRIPTION

Figure 1:
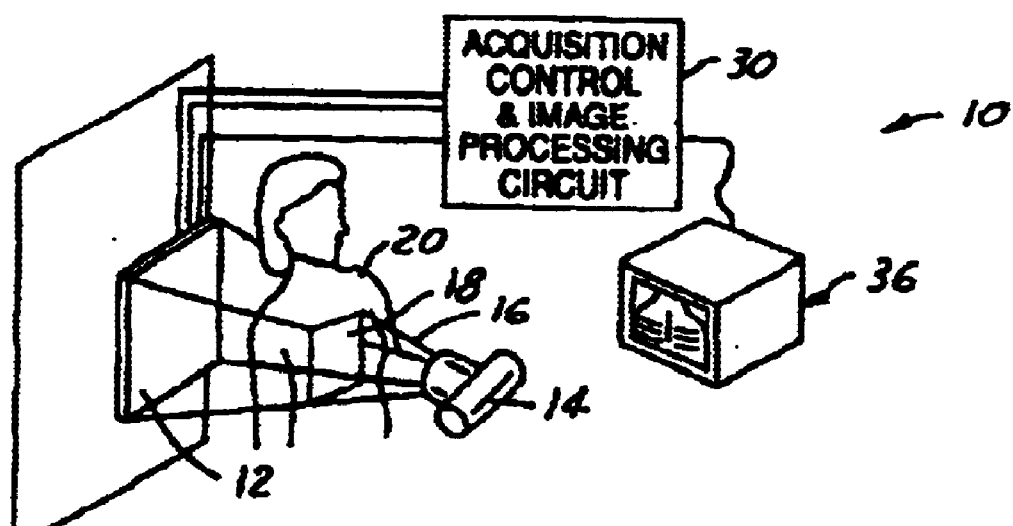
FIG. 1 is a perspective view of an imaging system according to one preferred embodiment of the present invention.

Referring now to FIG. 1, an imaging system (or detector) 10, for example, an X-ray imaging system, is shown including a photodetector array 12 and an X-ray source 14 collimated to provide an area X-ray beam 16 passing through an area 18 of a patient 20. Beam 16 is attenuated by an internal structure (not shown) of patient 20 to be received by detector array 12 which extends generally over an area in a plane perpendicular to the axis of the X-ray beam 16.

System 10 also includes an acquisition control and image-processing circuit 30 that is electrically connected to X-ray source 14 and detector array 12. More specifically, circuit 30 controls X-ray source 14, turning it on and off and controlling the tube current and thus the fluence of X-rays in beam 16 and/or the tube voltage and thereby altering the energy of the X-rays in beam 16. In one embodiment, the acquisition control and image processing circuit 30 includes a data acquisition system (DAS) having at least one DAS module, or circuit, which samples data from detector array 12 and transmits the data signals for subsequent processing. In one embodiment, each DAS module includes a plurality of driver channels or a plurality of readout channels. Acquisition control and image processing circuit 30 receives sampled X-ray data from DAS and generates image and displays the image on a monitor, or cathode-ray tube display 36 based on the data in each pixel 33.

Figure 2:
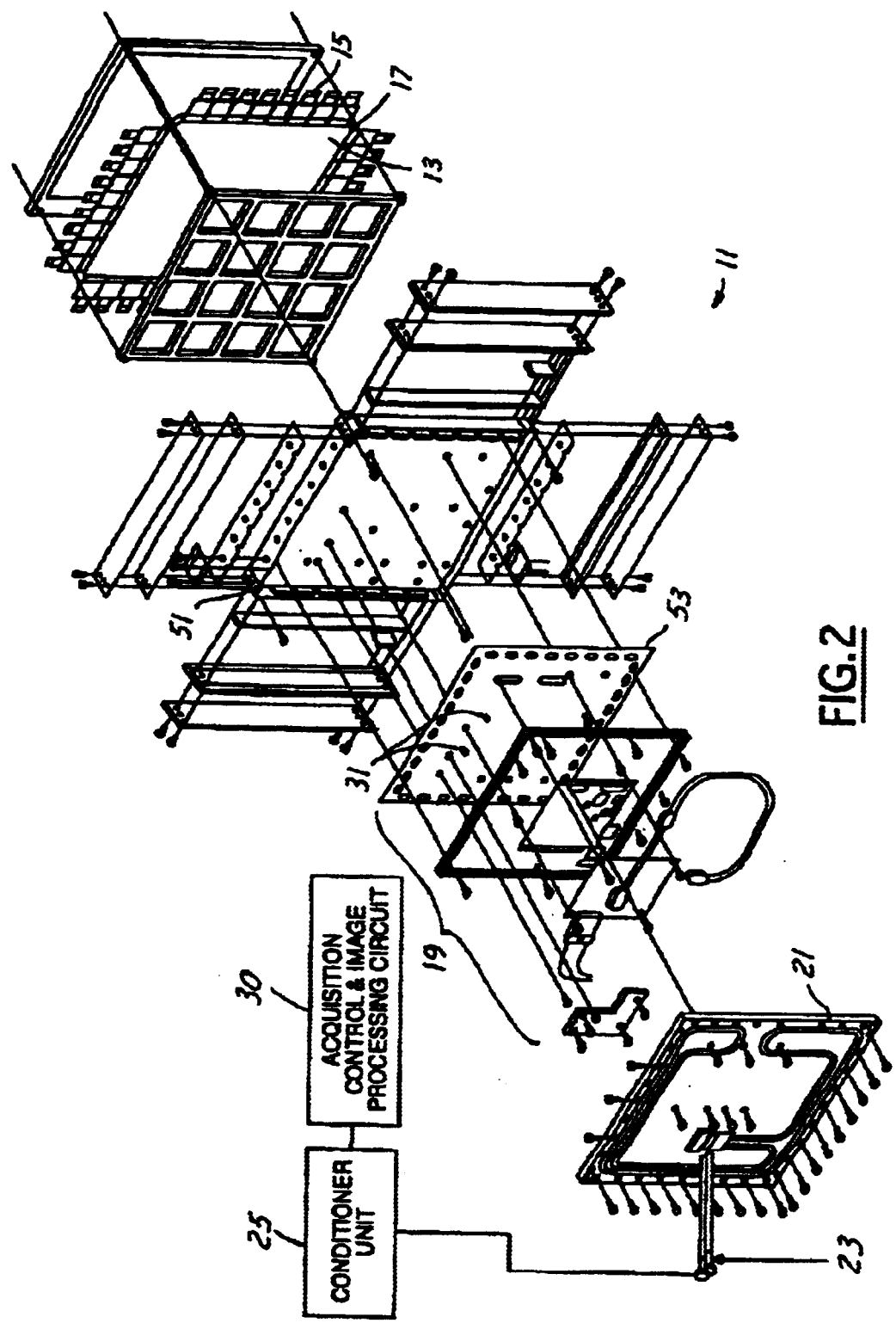
FIG. 2 is an exploded view of a portion of FIG. 1.

FIG. 2 depicts an exploded view of the detector assembly 11 according to a preferred embodiment of the present invention. The assembly 11 consists of a detector panel 13 having electronic modules 15 attached to the edges via flex connectors 17. Attached to the detector panel 13 is the detector array 12. Also coupled to the detector panel 13 is a circuit board 19 and a cold plate 21. The circuit board 19 is shown as having a reference regulator board 53. A mechanical structure 51 attaches the detector panel 13 and array 12 to the circuit board 19 and cold plate 21 and provides heat conduction paths from heat generating parts to the cold plate 21. The cold plate is connected to a conditioner unit 25 via a coolant connection 23.

The conditioner unit 25 provides temperature control for the imaging system 10. The conditioner unit 25 primarily functions to provide chilled coolant used to remove heat from heat generating parts, but can also function to provide heat to warm a detector 10 that is not up to operating temperatures. The coolant used within the conditioner unit 25 and coldplate 21 is typically distilled water with additives to retard corrosion and biological contamination, however antifreeze can be used in imaging systems 10 which may experience sub-freezing temperatures. A processing circuit 30 is coupled to the conditioner unit 25 and functions to control the temperature of the coolant exiting the conditioner unit 25.

Figure 3:
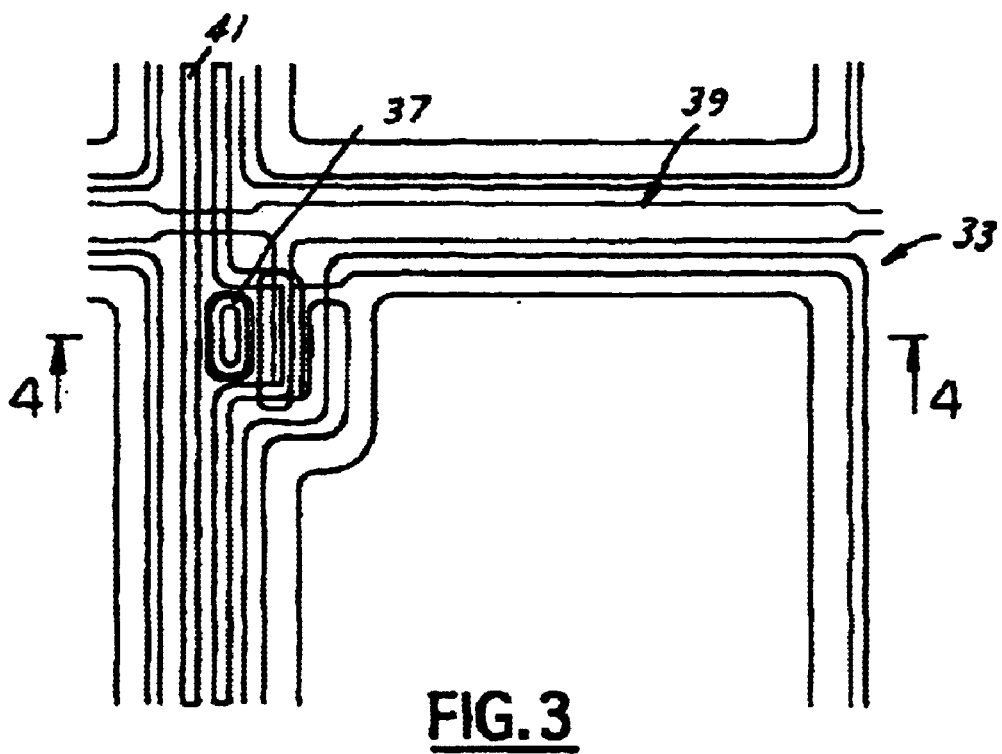
FIG. 3 is a plan view of the detector panel of FIG. 2 without the scintillator material.
Figure 4:
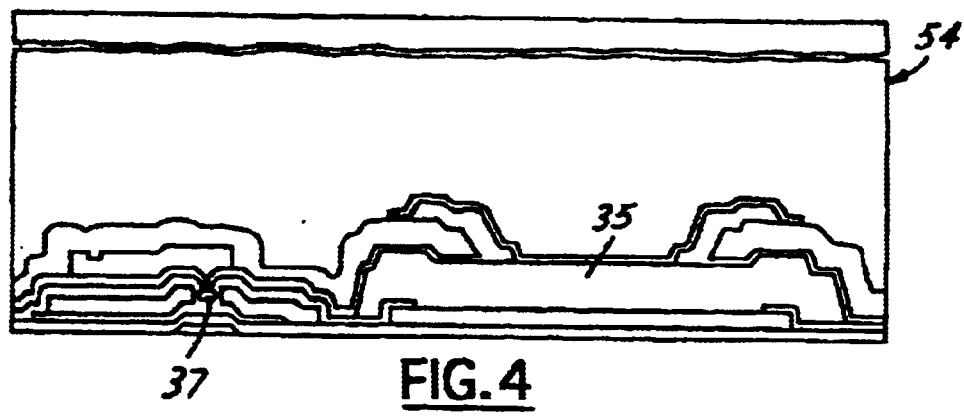
FIG. 4 is a section view of a FIG. 3 taken along line 4—4 showing the scintillator material.

Referring now to FIGS. 3 and 4, the detector array 12 is preferably fabricated in a solid-state panel configuration having a plurality of detector elements, or pixels 33 arranged in columns or rows. As will be understood by those of ordinary skill in the art, the orientation of the columns and rows is arbitrary; however, for clarity of description, it will be assumed that the rows extend horizontally and the columns extend vertically.

As best seen in FIG. 4, each pixel 33 includes a photosensor, such as a photodiode 35, that is coupled via a switching transistor 37 (field effect transistor, or FET) to two separate address lines, a scan line 39 and a data line 41. The radiation incident on a scintillator material 54 and the pixel 33 photosensors measure, by way of change in the charge across the photodiode 35, the amount of light generated by X-ray interaction with the scintillator 54. As a result, each pixel 33 produces an electrical signal that represents the intensity, after attenuation of patient 20, of an impinging X-ray beam 16.

Operating environment (temperature) is a concern for solid state X-ray detectors 10 because leakage may reduce dynamic range available to represent signal proportional to the absorption of light by the photodiode 35. The light produced by the scintillator directly above the photodiode 35 is proportional to the amount of X-ray photons absorbed by the scintillator. In general, higher temperature means higher diode 35 leakage. Higher leakage means, among other things, reduced available dynamic range and perhaps increased noise. Presently, separate temperature sensors 31, somewhat removed from the detector panel 13, are used to monitor the temperature of a small number of locations inside the detector assembly 11. The temperature set point of the conditioner unit 25 used to control the temperature is then adjusted based on these sensors 31. However, because the temperature sensors 31 are not in direct contact with the detector panel 13, and because the heat dissipation capacity of the circuit board 19 may affect the temperature sensors 31, the temperature of the detector panel 13 and spatial distribution across the detector panel 13 can only be known approximately.

It is presently necessary to correct images taken with the X-ray with an "offset image" taken without X-ray. The term "offset image" is used here to refer to an image taken from the X-ray detector 10 without X-ray illumination, and which represents the output of the detector 10 due to confounding factors. These confounding factors includes but are not limited to diode 35 leakage, charge retention, and electronic noise. For the purposes of the present invention, differences in digitized output values for a pixel's diode 35 in an offset image that correlate to differences in temperature of that pixel's diode 35 are considered primarily due to diode 35 leakage, which is also known as dark current because it is the current that the diode 35 is passing while not illuminated.

A more direct measure of the panel 13 temperature and a better representation of the spatial distribution of temperature across the panel 13 is therefore desired.

The present invention uses the dark current of the diodes 35 to sense temperature by determining their leakage from an offset image taken without X-ray either just before or just after the X-ray image is acquired and then calculating the temperature of each diode 35 by using parameters determined from prior measurements of the leakage of the diodes at known temperatures.

Figure 5:
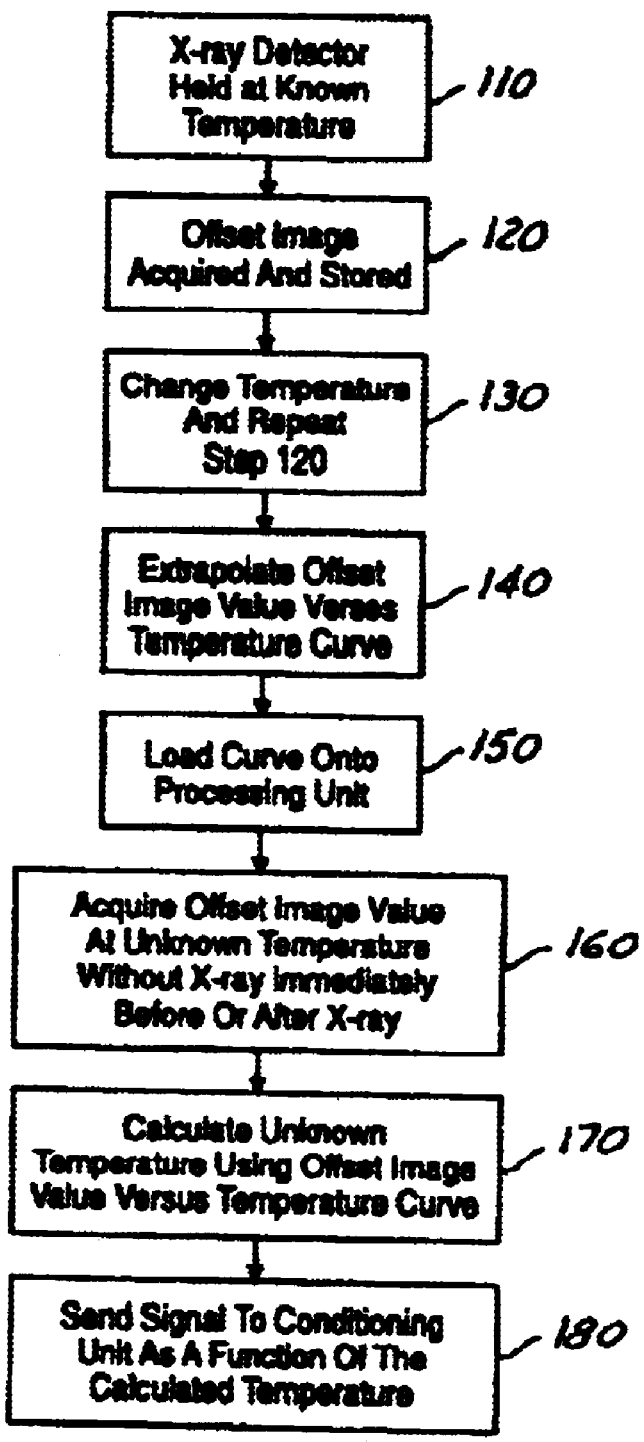
FIG. 5 is a logic flow diagram for preparing the detector panel and imaging system to determine detector panel temperature either immediately prior to or immediately after X-ray acquistion.

Referring now to FIG. 5, a logic flow diagram for preparing the X-ray detector panel 13 at the time of manufacture is illustrated. In Step 110, the X-ray detector panel 13 is held at a known temperature. Next, in Step 120, an offset image is acquired with no X-ray. Offset values for these offset images are recorded and stored in a processing circuit 30 for each diode 35 (pixel 33). The process is repeated at two or more temperatures in Step 130.

Next, in Step 140, for each pixel 33, the offset values at several temperatures are reduced to parametric coefficients within the processing unit. Thus, each pixel 33 has its own temperature versus offset curve. In Step 150, the data is loaded into the processing circuit 30 contained within the detector assembly 11 for use by the image acquisition software contained within the detector 11.

Next, in step 160, values from offset images acquired when the X-ray detector 10 is used, taken either directly before or directly after X-ray images are taken, are used with the temperature dependent coefficients on some or all of the diodes 35 on the panel 13. These offset values are then inputted in Step 170 into the temperature versus offset curve generated for each pixel 33 within the processing circuit 30 to calculate the temperature of the panel 13 at the time of offset image acquisition.

Finally, in Step 180, the temperature of the panel 13 and spatial distribution of temperature across the panel 13 can may be modified using the conditioner unit 25 coupled to the processing circuit 30 to maintain the panel within the temperature range required for imaging as a function of the acquired offset image received in Step 170. For example, if the acquired offset image corresponds to a temperature that is above the normal operating range, the processing circuit 30 directs the conditioner 25 to introduce chilled coolant to the coldplate 19 to decrease the temperature of the detector panel 13. Similarly, if the acquired offset image corresponds to a temperature that is below the normal operating range, the processing circuit 30 directs the conditioner 25 to introduce heated coolant to the coldplate 19 to increase the temperature of the detector panel 13.

The present invention provides more accurate data about the temperature of the X-ray detector panel 13 and spatial distribution of temperature across the panel 13, than is available in known X-ray detectors. Panel 13 temperature is directly sensed, rather than extrapolated from data from temperature sensors 31 that are not in direct contact with the panel 13. This will enable cooling to be better controlled. Also, this will enable use of other cooling methods not presently used such as direct conduction cooling with heat pumped by thermoelectric coolers. The present invention also eliminates the need for thermal sensors 31 on the circuit board 19, saving costs, simplifying designs, and potentially increasing reliability of the detector 10.

While one particular embodiment of the invention have been shown and described, numerous variations and alternative embodiments will occur to those skilled in the art. Accordingly, it is intended that the invention be limited only in terms of the appended claims.

What is claimed is:

1. A method for accurately determining temperature of a detector panel having a plurality of photodiodes in an X-ray imaging system at the time an X-ray image is taken comprising:

measuring an offset image value for at least one of the plurality of photodiodes of the detector panel taken for at least two known temperatures without X-ray;

extrapolating an offset image value versus temperature curve for each of said measured offset image values for each of said at least one of the plurality of photodiodes;

storing said extrapolated offset image value versus temperature curve for each of said plurality of photodiodes within a processing circuit, said processing circuit coupled within the X-ray imaging system; and determining the temperature of the detector panel immediately after use of the X-ray imaging system by measuring a second offset image value taken without an X-ray for said at least one of said plurality of photodiodes and comparing said second offset image value to said offset image value versus temperature curve.

2. The method of claim 1, wherein measuring said offset image value comprises measuring an offset image value without an X-ray for at least two known temperatures for a plurality of photodiodes contained on the detector panel prior to installation of said detector panel within the x-ray imaging system.

3. A method for directly controlling temperature of a detector panel of an X-ray imaging system having a plurality of photodiodes comprising:

providing a conditioner unit and a processing circuit and a coldplate, wherein said conditioner unit is fluidically coupled to said coldplate and electronically coupled to said processing circuit;

measuring an offset images value for at least one of the plurality of photodiodes of the detector panel taken for at least two known temperatures without X-ray;

extrapolating an offset image versus temperature curve for each of said measured offset image values for each of said at least one of the plurality of photodiodes;

storing said extrapolated offset image versus temperature curve for each of said plurality of photodiodes within said processing circuit;

determining the temperature of the detector panel immediately alter use of the X-ray imaging system by measuring a second offset image value taken without an X-ray for said at least one of said plurality of photodiodes and comparing said second offset image value to said offset image versus temperature curve; and directing an electrical signal from said processing circuit to said conditioner unit that correlates to the temperature of said detector panel determined from said second offset value, said electrical signal used by said conditioner wilt to control the temperature of coolant flowing to said coldplate to maintain said detector panel within a operating temperature range.

4. The method of via claim 3, wherein said electrical signal is used by said conditioner unit to also control the flow rate of coolant flowing to said coldplate as a function of said electrical signal.

5. The method of claim 3, wherein measuring said offset image value comprises measuring an offset image value for at least one of the plurality of photodiodes of the detector panel taken for at least two known temperatures without X-ray prior to installation of said detector panel within the x-ray imaging system.

6. The method of claim 3, wherein said conditioner unit decreases the temperature of coolant flowing to said coldplate when the temperature of said detector panel is above said operating temperature range.

7. The method of claim 6, wherein said conditioner unit increases the flow rate of the coolant flowing to said detector panel when the temperature of said detector panel is above said operating temperature range.

8. The method of claim 3, wherein said conditioner unit increases the temperature of coolant flowing to said coldplate when the temperature of said detector panel is below said operating temperature range as measured by said second offset value.

9. The method of claim 8, wherein said conditioner unit decreases the flow rate of the coolant flowing to said detector panel when the temperature of said detector panel is below said operating temperature range as measured by said second offset value.

10. A method for improving closed-loop control of cooling in an X-ray imaging system comprising:

determining an amount of photodiode leakage exhibited by at least one of a plurality of photodiodes immediately after X-ray images are taken;

controlling the coolant temperature of coolant flowing from a conditioner unit to a coldplate contained within the X-ray imaging system as a function of said amount of photodiode leakage.

11. The method of claim 10, wherein determining an amount of photoleakage comprises:

measuring an offset image value for at least one of the plurality of photodiodes of the detector panel taken for at least two known temperatures without X-ray;

extrapolating an offset image value versus temperature curve for each of said measured offset image values for each of said at least one of the plurality of photodiodes;

storing said extrapolated offset image value versus temperature curve for each of said plurality of photodiodes within a processing circuit;

determining the temperature of the detector panel immediately after use of the X-ray imaging system by measuring a second offset image value taken without an X-ray for said at least one of said plurality of photodiodes and comparing said second offset image value to said offset in-age value versus temperature curve.

12. An X-ray imaging system having a closed-loop cooling system comprising:

a detector panel having a plurality of photodiodes;

a coldplate closely coupled with said detector panel;

a processing circuit electrically coupled with at least one of said plurality of photodiodes said processing circuit capable of producing a signal representing the temperature of the detector panel as measured immediately after the acquisition of an X-ray by the X-ray imaging system by measuring the amount of dark current generated by said at least one of said plurality of photodiodes and determining the temperature of said detector panel located near said at least one of said plurality of photodiodes as a function of said amount of dark current; and a conditioner unit fluidically coupled with said coldplate and electrically coupled with said processing circuit, said conditioner unit capable of maintaining said detector panel within an operating temperature range.

13. The X-ray imaging system of claim 12, wherein said processing circuit has a stored offset image value versus temperature curve for each of said at least one of said plurality of photodiodes, said processing circuit capable of determining the temperature of said detector panel immediately prior to or immediately after acquiring an X-ray image by measuring an offset image value of said one of said plurality of photodiodes without an X-ray and converting said offset image value using said stored offset image value versus temperature curve to a temperature value representing the temperature of the detector panel, wherein said temperature value is subsequently converted to a signal by said processing circuit corresponding to the temperature of the detector panel.

14. The X-ray imaging system of claim 12, wherein an offset image value for each of said at least one of said plurality of photodiodes is measured for at least two known temperatures and stored within said stored offset image value versus temperature curve prior to installing said detector panel into the X-ray imaging system.

15. The X-ray imaging system of claim 12, wherein said conditioner unit decreases the temperature of coolant flowing to said coldplate from said conditioner unit when the temperature of said detector panel is above said operating temperature range.

16. The X-ray imaging system of claim 12, wherein said conditioner unit increases the flow rate of coolant flowing to said coldplate from said conditioner unit when the temperature of said detector panel is above said operating temperature range.

17. The X-ray imaging system of claim 12, wherein said conditioner unit increases the temperature of coolant flowing to said coldplate from said conditioner unit when the temperature of said detector panel is below said operating temperature range.

18. The X-ray imaging system of claim 12, wherein said conditioner unit decreases the flow rate of the coolant flowing to said detector panel when the temperature of said detector panel is below said operating temperature range.

* * * * *